United States Patent [19]
Holton et al.

[11] Patent Number: 5,284,864
[45] Date of Patent: Feb. 8, 1994

[54] BUTENYL SUBSTITUTED TAXANES AND PHARMACEUTICAL COMPOSITIONS CONTAINING THEM

[75] Inventors: Robert A. Holton; Hossain Nadizadeh, both of Tallahassee, Fla.

[73] Assignee: Florida State University, Tallahassee, Fla.

[21] Appl. No.: 975,705

[22] Filed: Nov. 13, 1992

Related U.S. Application Data

[63] Continuation-in-part of Ser. No. 949,107, Sep. 22, 1992, which is a continuation-in-part of Ser. No. 863,849, Apr. 6, 1992, abandoned, which is a continuation-in-part of Ser. No. 862,955, Apr. 3, 1992, abandoned, which is a continuation-in-part of Ser. No. 763,805, Sep. 23, 1991, abandoned.

[51] Int. Cl.$^5$ .................. A61K 31/335; C07D 305/14
[52] U.S. Cl. ........................ 514/449; 544/60; 544/147; 544/375; 546/196; 546/207; 548/525; 549/214; 549/510; 549/511
[58] Field of Search ........ 549/510, 511, 214; 544/60, 147, 375; 546/196, 207; 548/525; 514/449

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,924,011 | 5/1990 | Denis et al. | 849/510 |
| 4,924,012 | 5/1990 | Colin et al. | 849/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,059,699 | 10/1991 | Kingston et al. | 549/511 |
| 5,136,060 | 8/1992 | Holton | 549/510 |
| 5,175,315 | 12/1992 | Holton | 549/510 |

FOREIGN PATENT DOCUMENTS

| | | |
|---|---|---|
| 253738 | 7/1987 | European Pat. Off. . |
| 253739 | 7/1987 | European Pat. Off. . |
| 336840 | 4/1989 | European Pat. Off. . |
| 336841 | 4/1989 | European Pat. Off. . |
| 247378 | 9/1990 | European Pat. Off. . |

WO92/09589 6/1992 PCT Int'l Appl. .

OTHER PUBLICATIONS

Denis and Greene, "A Highly Efficient Practical Approach to Natural Taxol", J. Am. Chem. Soc. 1988, 110, 5917-5919.

Holton et al., "A Synthesis of Taxusin", J. Am. Chem. Soc., 1988, 110, pp. 6558-6560.

Holton, "Synthesis of the Taxane Ring System", J. Am. Chem. Soc., 1984, 106, pp. 5731-5732.

(List continued on next page.)

Primary Examiner—C. Warren Ivy
Assistant Examiner—Ba K. Trinh
Attorney, Agent, or Firm—Senniger, Powers, Leavitt & Roedel

[57] ABSTRACT

Taxane derivatives of the formula

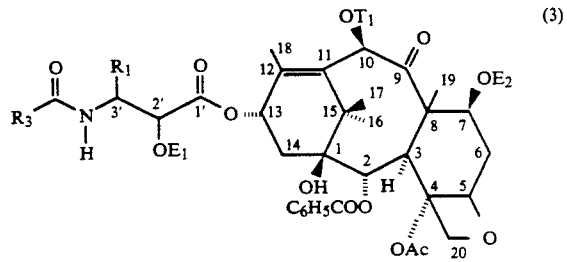

(3)

wherein
$R_1$ is butenyl,
$R_3$ is phenyl,
$T_1$ is hydrogen, hydroxyl protecting group, or $-COT_2$,
$T_2$ is H, $C_1-C_6$ alkyl, $C_2-C_6$ alkenyl, $C_2-C_6$ alkynyl or monocylic aryl,
Ac is acetyl, and
$E_1$ and $E_2$ are independently selected from hydrogen and functional groups which increase the water solubility of the taxane derivative are useful as antitumor agents.

6 Claims, No Drawings

OTHER PUBLICATIONS

Mukerjee et al., "β-Lactams: Retrospect and Prospect", Tetrahedron vol. 34, Report No. 52, pp. 1731–1767 (1978).

Wani et al., "Plant Antitumor Agents. VI. The Isolation and Structure of Taxol, a Novel Antileukemic and Antitumor Agent from *Taxus brevifolia*", J. Am. Chem. Soc. 93:9, May 5, 1971, pp. 2325–2327.

Samaranayake et al., "Modified Taxols. 5.1 Reaction of Taxol with Electrophilic Reagents and Preparation of a Rearranged Taxol Derivative with Tubulin Assembly Activity3.", J. Org. Chem. 1991, 56, 5114–5119.

Kaiser et al., "Synthesis of Esters of Acid-Unstable Alcohols by Means of n-butyllithium", J. Org. Chem., 1970, 35, 1198.

Ojima et al., "New and Efficient Approaches to the Semisynthesis of Taxol and its C-13 Side Chain Analogs by Means of β-Lactam Synthon Method", Tetrahedron vol. 48, No. 34, pp. 6985–7012, 1992.

Witherup et al., "High Performance Liquid Chromatographic Separation of Taxol and Related Compounds From *Taxus brevifolia*", Jour. of Liquid Chromatography, 12(11), pp. 2117–2132 (1989).

Bartholomew et al., "A Novel Rearrangement Reaction Conversion of 3-(chloromethyl)azetidin-2-ones to Azetidine-3-carboxylic Acid Esters", Tetrahedron Letters, vol. 32, No. 36, pp. 4795–4798, 1991.

Schultz et al., "Synthesis of New N-radicals of Tetrazan-1-yl", Chem. Abstr., vol., 108, No. 37298C, pp. 581, 1988.

H. M. Deutsch et al., "Synthesis of Congeners and Prodrugs. 3. Water-Soluble Prodrugs of Taxol with Potent Antitumour Activity", Journal of Medicinal Chem., vol. 32, No. 4, pp. 788–792, (Apr. 1989).

N. F. Magri et al., "Modified Taxols, 4. Synthesis and Biological Activity of Taxols Modified in the Side Chain", vol. 51, No. 2, pp. 298–306, (1988).

V. Senilh et al., "Hemisynthese de nouveaux analogues du taxol. Etude de leur interaction avec lat tubuline", C. R. Acad. Sc. Paris, Serie II, vol. 299, No. 15, pp. 1039–1043, Nov. 21, 1984.

BUTENYL SUBSTITUTED TAXANES AND PHARMACEUTICAL COMPOSITIONS CONTAINING THEM

REFERENCE TO RELATED APPLICATIONS

This application is a continuation-in-part application of U.S. Ser. No. 07/949,107, filed Sep. 22, 1992, now pending, which is a continuation-in-part application of U.S. Ser. No. 07/863,849, filed Apr. 6, 1992, now abandoned, which is a continuation-in-part application of U.S. Ser. No. 07/862,955, filed Apr. 3, 1992, now abandoned, which is a continuation-in-part of U.S. Ser. No. 07/763,805, filed Sep. 23, 1991, now abandoned.

BACKGROUND OF THE INVENTION

The present invention is directed to novel taxanes which have utility as antileukemia and antitumor agents.

The taxane family of terpenes, of which taxol is a member, has attracted considerable interest in both the biological and chemical arts. Taxol is a promising cancer chemotherapeutic agent with a broad spectrum of antileukemic and tumor-inhibiting activity. Taxol has a 2'R, 3'S configuration and the following structural formula:

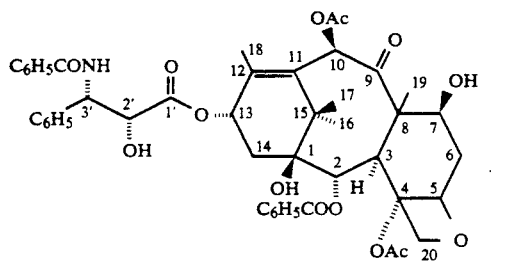

wherein Ac is acetyl. Because of this promising activity, taxol is currently undergoing clinical trials in both France and the U.S.

Colin et al. reported in U.S. Pat. No. 4,814,470 that taxol derivatives having structural formula (2) below, have an activity significantly greater than that of taxol (1).

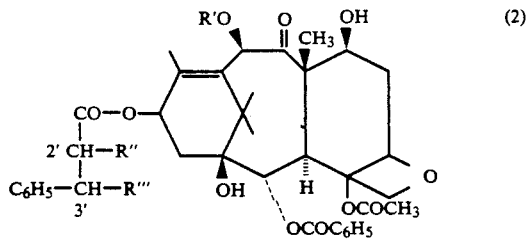

R' represents hydrogen or acetyl and one of R" and R'" represents hydroxy and the other represents tert-butoxycarbonylamino and their stereoisomeric forms, and mixtures thereof. The compound of formula (2) in which R" is hydroxy, R'" is tert-butoxycarbonylamino having the 2'R, 3'S configuration is commonly referred to as taxotere.

Although taxol and taxotere are promising chemotherapeutic agents, they are not universally effective. Accordingly, a need remains for additional chemotherapeutic agents.

SUMMARY OF THE INVENTION

Among the objects of the present invention, therefore, is the provision of novel taxane derivatives which are valuable antileukemia and antitumor agents.

Briefly, therefore, the present invention is directed to taxane derivatives of the formula:

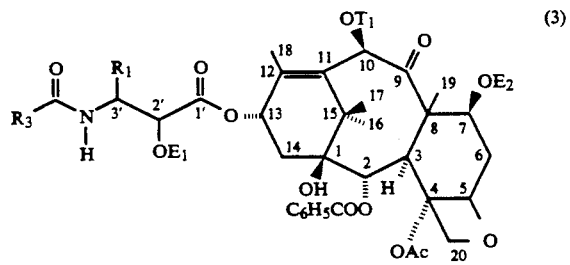

wherein
$R_1$ is butenyl,
$R_3$ is phenyl,
$T_1$ is hydrogen, hydroxyl protecting group, or $-COT_2$,
$T_2$ is H, $C_1-C_6$ alkyl, $C_2-C_6$ alkenyl, $C_2-C_6$ alkynyl or monocylic aryl,
Ac is acetyl, and
$E_1$ and $E_2$ are independently selected from hydrogen, hydroxy protecting groups and functional groups which increase the water solubility of the taxane derivative.

Other objects and features of this invention will be in part apparent and in part pointed out hereinafter.

DETAILED DESCRIPTION OF THE PREFERRED EMBODIMENTS

In accordance with the present invention, it has been discovered that compounds having structural formula (3), in general, and structural formula (4), in particular, show remarkable properties, in vitro, and are valuable antileukemia and antitumor agents. Their biological activity has been determined in vitro, using tubulin assays according to the method of Parness et al., *J. Cell Biology*, 91: 479–487 (1981) and human cancer cell lines, and is comparable to that exhibited by taxol and taxotere.

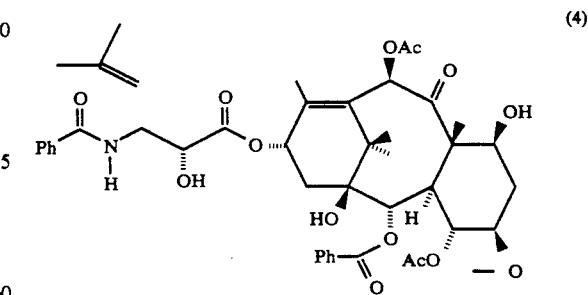

Taxane (4) which has the 2'R, 3'S configuration may be obtained by reacting a β-lactam with metal alkoxides having the taxane tetracyclic nucleus and a C-13 metallic oxide substituent to form compounds having a β-amido ester substituent at C-13. The β-lactams have the following structural formula:

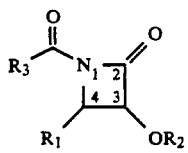

wherein

R$_1$ is butenyl,

R$_2$ is a hydroxy protecting group, and

R$_3$ is phenyl.

β-lactams (5) can be prepared from readily available starting materials, as is illustrated by the following reaction scheme:

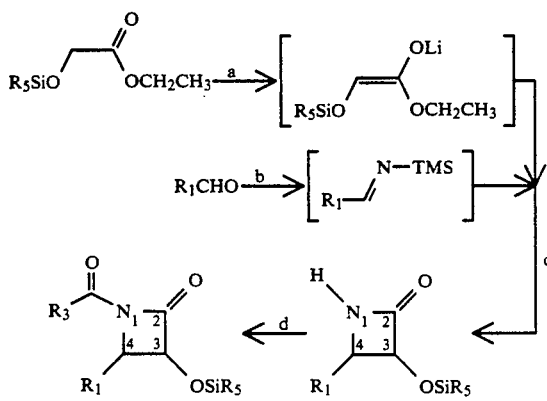

reagents (a) lithium diisopropyl amide, tetrahydrofuran ("THF"), −78° C. to −50° C.;

(b) lithium hexamethyl disilazane, THF, −78° C. to 0° C.;

(c) THF, −78° C. to 25° C., (2h); and (d) triethylamine and benzoyl chloride.

The 3-hydroxyl protecting group shown in the above reaction scheme is —SiR$_5$ wherein R$_5$ is trialkyl or triaryl such as triethyl. The 3-hydroxyl may be protected with other standard protecting groups such as 1-ethoxyethyl, or 2,2,2-trichloroethoxymethyl. Additional hydroxy protecting groups and the synthesis thereof may be found in "Protective groups in Organic Synthesis" by T. W. Greene, John Wiley & Sons, 1981.

The racemic β-lactams may be resolved into the pure enantiomers prior to protection by recrystallization of the corresponding 2-methoxy-2-(trifluoromethyl) phenylacetic esters. However, the reaction described hereinbelow in which the β-amido ester side chain is attached hasthe advantage of being highly diastereoselective, thus permitting the use of a racemic mixture of side chain precursor.

The metal alkoxides having the taxane tetracyclic nucleus and a C-13 metallic oxide substituent have the following structural formula:

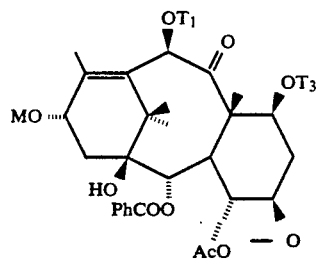

wherein T$_1$ is hydrogen, hydroxyl protecting group, or —COT$_2$; T$_2$ is H, C$_1$–C$_6$ alkyl, C$_2$–C$_6$ alkenyl, C$_2$–C$_6$ alkynyl or monocylic aryl; T$_3$ is hydrogen or a hydroxy protecting group; and M is a metal, preferably selected from the group comprising Group IA, Group IIA and transition metals, most preferably, Li, Mg, Na, K or Ti.

Preferably, the metal alkoxides are prepared by reacting an alcohol having the taxane tetracyclic nucleus and a C-13 hydroxyl group with an organometallic compound in a suitable solvent. Most preferably, the alcohol is a protected baccatin III, in particular, 7-O-triethylsilyl baccatin III (which can be obtained as described by Greene, et al. in *JACS* 110: 5917 (1988) or by other routes) or 7,10-bis-O-triethylsilyl baccatin III.

As reported in Greene et al., 10-deacetyl baccatin III is converted to 7-O-triethylsilyl-10-deacetyl baccatin III according to the following reaction scheme:

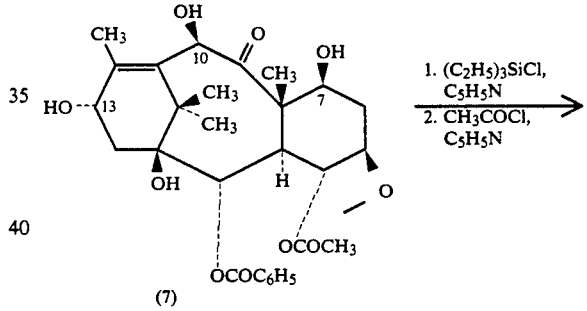

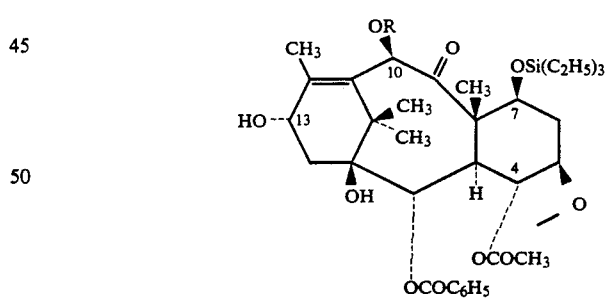

(8) a, T$_1$ = H
    b, T$_1$ = COCH$_3$

Under what is reported to be carefully optimized conditions, 10-deacetyl baccatin III is reacted with 20 equivalents of (C$_2$H$_5$)$_3$SiCl at 23° C. under an argon atmosphere for 20 hours in the presence of 50 ml of pyridine/mmol of 10-deacetyl baccatin III to provide 7-triethylsilyl-10-deacetyl baccatin III (8a) as a reaction product in 84–86% yield after purification. The reaction product may then optionally be acetylated with 5 equivalents of CH$_3$COCl and 25 mL of pyridine/mmol of 8a at 0° C. under an argon atmosphere for 48 hours to provide 86% yield of 7-O-triethylsilyl baccatin III (8b). Greene, et al. in JACS 110, 5917 at 5918 (1988).

The 7-O-triethylsilyl baccatin III (8b) is reacted with an organometallic compound such as n-butyllithium in a solvent such as tetrahydrofuran (THF), to form the metal alkoxide 13-O-lithium-7-O-triethylsilyl baccatin III (9) as shown in the following reaction scheme:

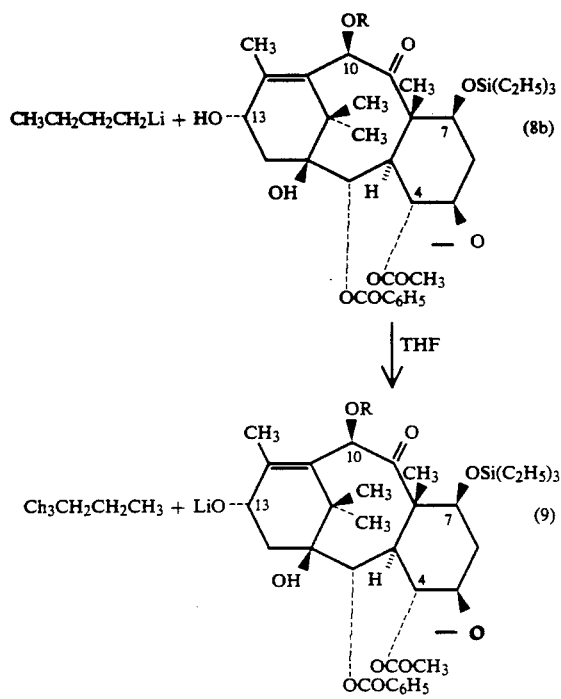

As shown in the following reaction scheme, 13-O-lithium-7-O-triethylsilyl baccatin III (9) reacts with β-lactam (5) in which R₂ is triethyl silyl to provide an intermediate in which the C-7 and C-2' hydroxyl groups are protected with a triethylsilyl group. The triethylsilyl groups are then hydrolyzed under mild conditions so as not to disturb the ester linkage or the taxane substituents.

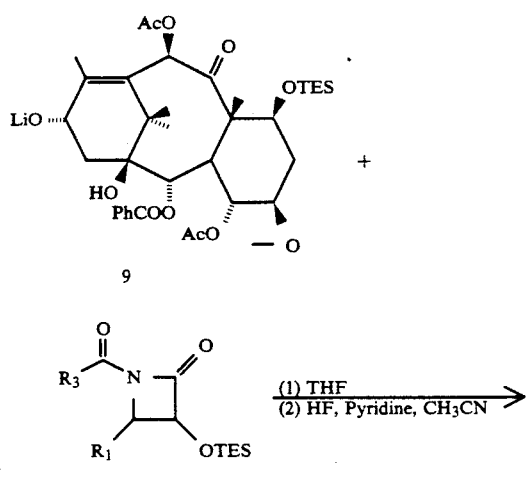

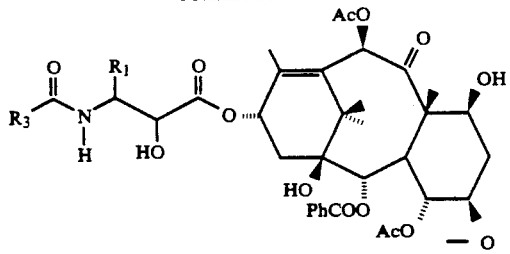

wherein
$R_1$ is butenyl, and
$R_3$ is phenyl.

Both the conversion of the alcohol to the metal alkoxide and the ultimate synthesis of the taxane derivative can take place in the same reaction vessel. Preferably, the β-lactam is added to the reaction vessel after formation therein of the metal alkoxide.

Compounds of formula (1) of the instant invention are useful for inhibiting tumor growth in animals including humans and are preferably administered in the form of a pharmaceutical composition comprising an effective anti-tumor amount of compound of the instant invention in combination with a pharmaceutically acceptable carrier or diluent.

Antitumor compositions herein may be made up in any suitable form appropriate for desired use; e.g., oral, parenteral or topical administration. Examples of parenteral administration are intramuscular, intravenous, intraperitoneal, rectal and subcutaneous administration.

The diluent or carrier ingredients should not be such as to diminish the therapeutic effects of the antitumor compounds.

Suitable dosage forms for oral use include tablets, dispersible powders, granules, capsules, suspensions, syrups, and elixirs. Inert diluents and carriers for tablets include, for example, calcium carbonate, sodium carbonate, lactose and talc. Tablets may also contain granulating and disintegrating agents such as starch and alginic acid, binding agents such as starch, gelatin and acacia, and lubricating agents such as magnesium stearate, stearic acid and talc. Tablets may be uncoated or may be coated by unknown techniques; e.g., to delay disintegration and absorption. Inert diluents and carriers which may be used in capsules include, for example, calcium carbonate, calcium phosphate and kaolin. Suspensions, syrups and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions and the like. They may also be manufactured in the form of sterile solid compositions which can be dissolved or suspended in sterile injectable medium immediately before use. They may contain suspending or dispersing agents known in the art.

The water solubility of compounds of formula (3) may be improved by modification of the C2' and/or C7 substituents to incorporate appropriate functional groups, $E_1$ and $E_2$. For increased water solubility, $E_1$ and $E_2$ may independently be hydrogen and —COG-COR¹ wherein G is ethylene, propylene, —CH=CH—, 1,2-cyclohexane, or 1,2-phenylene, R¹ = OH base, NR²R³, OR³, SR³, OCH²CONR⁴R⁵, or OH
R² = hydrogen, methyl
R³ = (CH₂)ₙNR⁶R⁷; (CH₂)ₙN⊕R⁶R⁷R⁸X⊖
n = 1 to 3
R⁴ = hydrogen, lower alkyl containing 1 to 4 carbons
R⁵ = hydrogen, lower alkyl containing 1 to 4 carbons, benzyl, hydroxyethyl, CH₂CO₂H, dimethylaminoethyl
R⁶R⁷ = lower alkyl containing 1 or 2 carbons, benzyl or R⁶ and
R⁷ together with the nitrogen atom of NR⁶R⁷ form the following rings

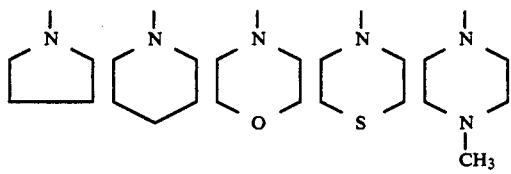

R⁸ = lower alkyl containing 1 or 2 carbons, benzyl
X⊖ = halide
base = NH₃, (HOC₂H₄)₃N, N(CH₃)₃, CH₃N(C₂H₄OH)₂, NH₂(CH₂)₆NH₂, N-methylglucamine, NaOH, KOH.

The preparation of compounds in which X₁ or X₂ is —COGCOR¹ is set forth in Hangwitz U.S. Pat. No. 4,942,184 which is incorporated herein by reference.

The following examples illustrate the invention.

EXAMPLE 1

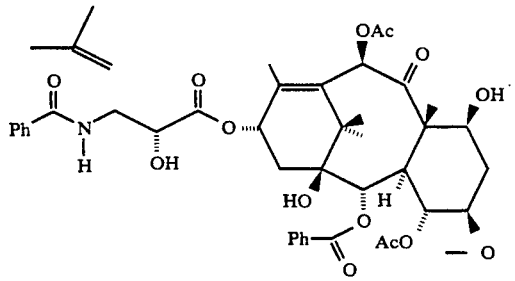

(4)

Preparation of 3'-desphenyl-3'-(2-methyl-1-propenyl) taxol.

To a solution of 7-triethylsilyl baccatin III (120 mg, 0.171 mmol) in 1.2 mL of THF at −45° C. was added dropwise 0.104 mL of a 1.63M solution of nBuLi in hexane. After 0.5 h at −45° C., a solution of cis-1-benzoyl-3-triethylsilyloxy-4-(2-methyl-1-propenyl)azetidin-2-one (295 mg, 0.885 mmol) in 1.2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 179 mg of a mixture containing (2'R,3'S)-2', 7-(bis)triethylsilyl-3'-desphenyl-3'-(2-methyl-1-propenyl) taxol and a small amount of the (2'S,3'R) isomer.

To a solution of 179 mg (0.171 mmol) of the mixture obtained from the previous reaction in 11 mL of acetonitrile and 0.55 mL of pyridine at 0° C. was added 1.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 140 mg of material which was purified by flash chromatography to give 109.0 mg (78%) of 3'-desphenyl-3'-(2-methyl-1-propenyl) taxol, which was recrystallized from methanol/water. m.p. 143°–144° C.; $[\alpha]^{25}_{Na}$ −61.0° (c 0.0065, CHCl₃).

¹H NMR (CDCl₃, 300 MHz) δ 8.11(d, J=7.1 Hz, 2H, benzoate ortho), 7.69(d, J=8.3 Hz, 2H, benzamide ortho), 7.64–7.36(m, 6H, aromatic), 6.45(d, J=8.2 Hz, 1H, NH), 6.29(s, 1H, H10), 6.20 (dd, J=7.7, 7.7 Hz, 1H, H13), 5.68(d, J=7.1 Hz, 1H, H2β), 5.46(m, 1H, vinyl), 5.27(ddd, J=8.8, 8.8, 3.3 Hz, 1H, H3'), 4.96 (d, J=7.7 Hz, 1H, H5), 4.40(m, 1H, H7), 4.36(m, 1H, H2'), 4.32(d, J=7.8 Hz, 1H, H20α), 4.22 (d, J=7.8 Hz, 1H, H20β), 3.82(d, J=7.1 Hz, 1H, H3), 3.63(d, J=6.6 Hz, 1H, 2'OH), 2.54(m, 1H, H6α), 2.48(d, J=3.9 Hz, 1H, 7OH), 2.42(m, 2H, H14), 2.39(s, 3H, 4Ac), 2.23 (s, 3H, 10Ac), 2.16(br s, 3H, Me18), 1.89 (m, 1H, H6β), 1.88 (s, 3H, Me19), 1.80(s, 4H, Me thienyl+1OH), 1.24(s, 3H, Me17), 1.14(s, 3H, Me16).

EXAMPLE 2

Tubulin binding assays were performed using compound (4) substantially as set forth in Parness et al., *J. Cell Biology* 91: 479–487 (1981) and compared to taxol and taxotere. The results are presented in Table 1.

TABLE 1

| Compound Name/Formula | Tubulin Assay | |
|---|---|---|
| | Init. Peak | Rel. Rate |
| 4 | 126 | — |
| Taxol | 100 | 98 |
| Taxotere | 100 | — |

EXAMPLE 4

Taxane (4) was evaluated in in vitro cytotoxicity activity against human colon carcinoma cells HCT-116 and HCT-116/VM46. The HCT116/VM cells are cells that have been selected for teniposide resistance and express the multidrug resistance phenotype, including resistance to taxol. Cytotoxicity was assessed in HCT116 and HCT VM46 human colon carcinoma cells by XTT (2,3-bis(2-methoxy-4-nitro-5-sulfophenyl)-5-[(phenylamino)carbonyl]-2H-tetrazolium hydroxide) assay (Scudiero et al, "Evaluation of a soluble tetrazolium/formazan assay for cell growth and drug sensitivity in culture using human and other tumor cell lines", *Cancer Res.* 48:4827–4833, 1988). Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance the greater the number of live cells. The results are expressed as an IC₅₀ which is the drug concentration required to inhibit cell proliferation (i.e. absorbance at 450 nm) to 50% of that of untreated control cells. The results are presented in Table 2. Lower numbers indicate greater activity.

TABLE 2

| Compound Name/Formula | IC$_{50}$ HCT 116 | HCT VM46 |
|---|---|---|
| 4 | 0.001 | 0.026 |
| Taxol | 0.004 | 0.536 |
| Taxotere | 0.007 | 0.246 |

In view of the above, it will be seen that the several objects of the invention are achieved.

As various changes could be made in the above compositions without departing from the scope of the invention, it is intended that all matter contained in the above description be interpreted as illustrative and not in a limiting sense.

We claim:

1. A taxane derivative of the formula

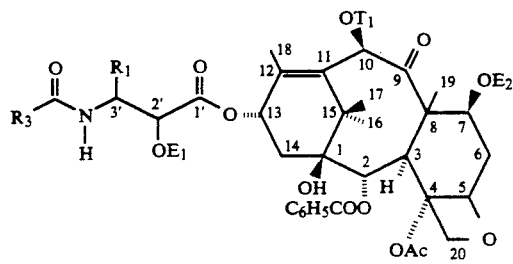

wherein
$R_1$ is butenyl,
$R_3$ is phenyl,
$T_1$ is hydrogen, hydroxyl protecting group, or —COT$_2$,
$T_2$ is H, $C_1$-$C_6$ aklyl, $C_2$-$C_6$ alkenyl, $C_2$-$C_6$ alkynyl or monocylic aryl,
Ac is acetyl, and
$E_1$ and $E_2$ are independently selected from hydrogen and hydroxyl protecting groups.

2. A taxane derivative of the formula

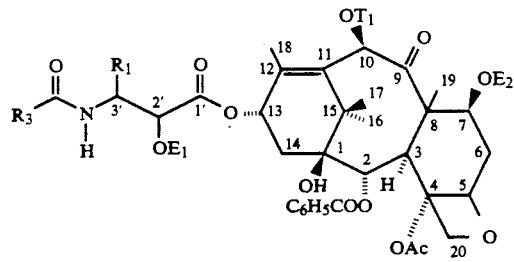

wherein
$R_1$ is butenyl,
$R_3$ is phenyl,
$T_1$ is hydrogen, hydroxyl protecting group, or —COT$_2$,
$T_2$ is H, $C_1$-$C_6$ alkyl, $C_2$-$C_6$ alkenyl, $C_2$-$C_6$ alkynyl or monocylic aryl,
Ac is acetyl, and
$E_1$ and $E_2$ are independently selected from hydrogen, and —COGCOR$^1$ wherein
G is ethylene, propylene, CH=CH, 1,2-cyclohexane, or 1,2-phenylene,
$R^1$=OH base, NR$^2$R$^3$, OR$^3$, SR$^3$, OCH$_2$CONR$^4$R$^5$, OH
$R^2$=hydrogen, methyl
$R^3$=(CH$_2$)$_n$NR$^6$R$^7$; (CH$_2$)$_n$N$\oplus$R$^6$R$^7$R$^8$X$\ominus$
n=1 to 3
$R^4$=hydrogen, lower alkyl containing 1 to 4 carbons
$R^5$=Hydrogen, lower alkyl containing 1 to 4 carbons, benzyl, hydroxyethyl, CH$_2$CO$_2$H, dimethylaminoethyl
$R^6R^7$=lower alkyl containing 1 or 2 carbons, benzyl or $R^6$ and
$R^7$ together with the nitrogen atom of NR$^6$R$^7$ form the following rings

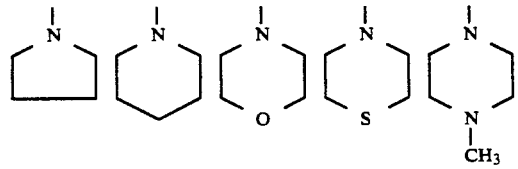

$R^8$=lower alkyl containing 1 or 2 carbons, benzyl
X$\ominus$=halide
base=NH$_3$, (HOC$_2$H$_6$)$_3$N, N(CH$_3$)$_3$, CH$_3$N(C$_2$H$_4$OH)$_2$, NH$_2$(CH$_2$)$_6$NH$_2$, N-methylglucamine, NaOH, KOH.

3. The taxane derivative of claim 1 wherein $T_1$ is —COCH$_3$, and $E_1$ and $E_2$ are hydrogen.

4. The taxane derivative of claim 1 wherein the taxane derivative has the 2'R, 3'S configuration.

5. A taxane derivative of the formula

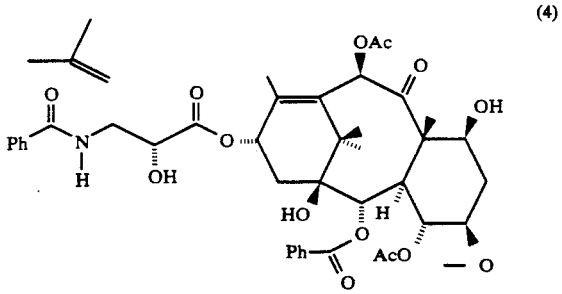

(4)

wherein
Ph is phenyl, and
Ac is acetyl.

6. A pharmaceutical composition which contains the taxane derivative of claim 1 and one or more pharmacologically acceptable, inert or physiologically active diluents or adjuvants.

* * * * *

UNITED STATES PATENT AND TRADEMARK OFFICE
CERTIFICATE OF CORRECTION

PATENT NO. : 5,284,864
DATED : February 8, 1994
INVENTOR(S) : Robert A. Holton and Hossain Nadizadeh It is certified that error appears in the above-identified patent and that said Letters Patent is hereby corrected as shown below:

In column 2, lines 50-60, the chemical structure (4) should read:

(4)

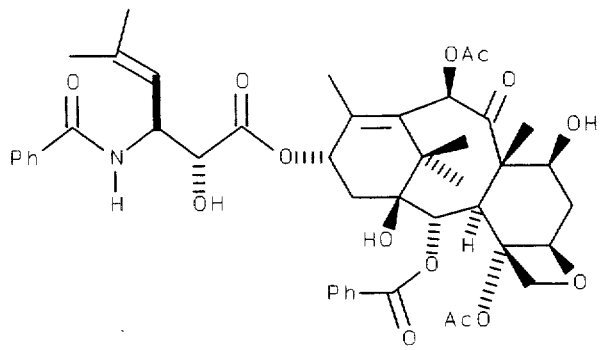

In column 4, lines 1-10, the chemical structure (6) should read:

(6)

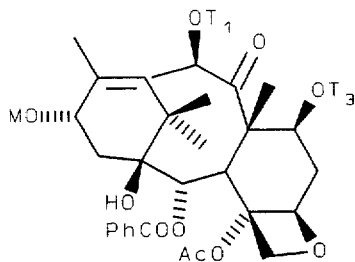

UNITED STATES PATENT AND TRADEMARK OFFICE
CERTIFICATE OF CORRECTION

PATENT NO. : 5,284,864
DATED : February 8, 1994
INVENTOR(S) : Robert A. Holton and Hossain Nadizadeh It is certified that error appears in the above-identified patent and that said Letters Patent is hereby corrected as shown below:

In column 4, lines 32-55 the chemical structures (7) and (8) should read:

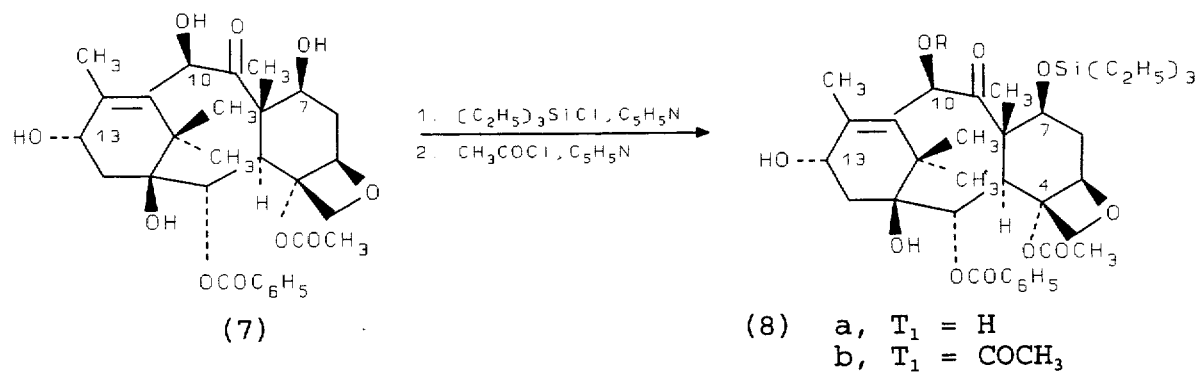

In column 5, lines 11-36, the chemical structures (8b) and (9) should read:

UNITED STATES PATENT AND TRADEMARK OFFICE
CERTIFICATE OF CORRECTION

PATENT NO. : 5,284,864

DATED : February 8, 1994

INVENTOR(S) : Robert A. Holton and Hossain Nadizadeh

It is certified that error appears in the above-identified patent and that said Letters Patent is hereby corrected as shown below:

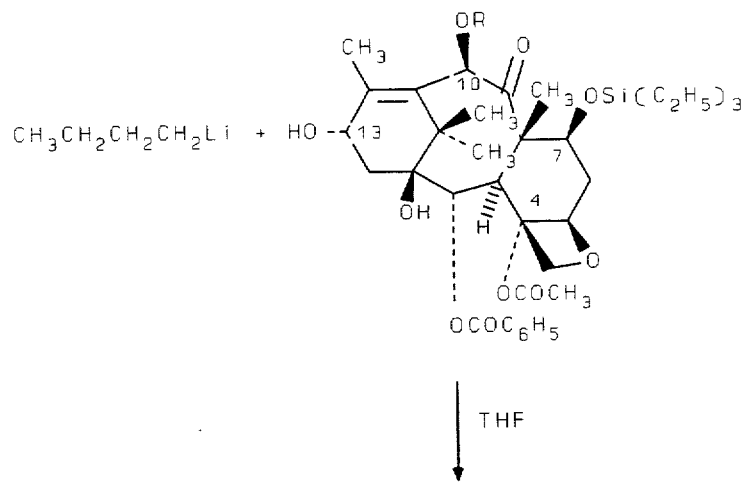

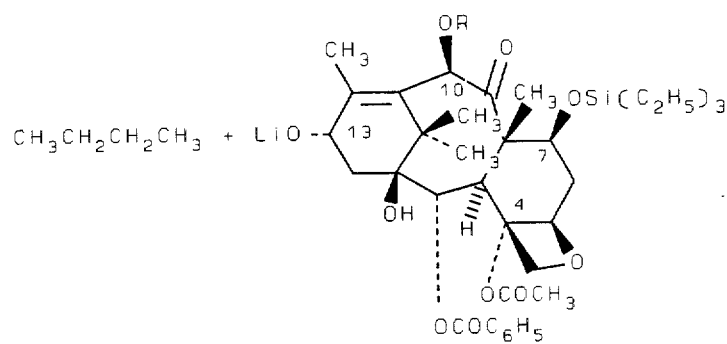

UNITED STATES PATENT AND TRADEMARK OFFICE
CERTIFICATE OF CORRECTION

PATENT NO. : 5,284,864
DATED : February 8, 1994
INVENTOR(S) : Robert A. Holton and Hossain Nadizadeh It is certified that error appears in the above-identified patent and that said Letters Patent is hereby corrected as shown below:

In column 5, lines 50-65 and column 6, lines 1-10, the chemical structures should read:

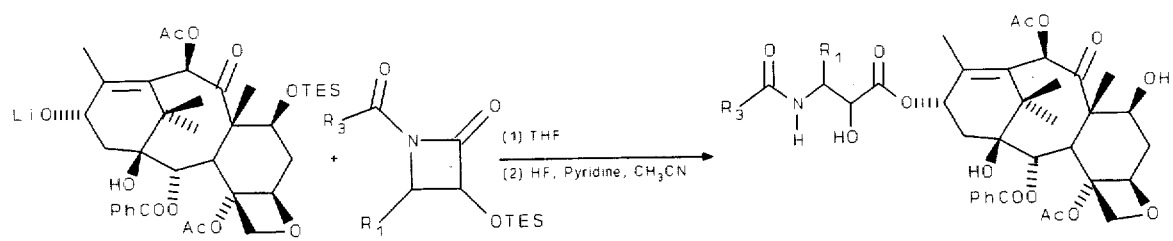

In column 7, line 4, "$(CH_2)_nN\oplus R^6R^7R^8X\ominus$" should read -- $(CH_2)_nN^{\oplus}R^6R^7R^8X^{\ominus}$ --.

In column 7, line 24, "$X\ominus$" should read -- $X^{\ominus}$ --.

UNITED STATES PATENT AND TRADEMARK OFFICE
CERTIFICATE OF CORRECTION

PATENT NO. : 5,284,864
DATED : February 8, 1994
INVENTOR(S) : Robert A. Holton and Hossain Nadizadeh It is certified that error appears in the above-identified patent and that said Letters Patent is hereby corrected as shown below:

In column 7, lines 35-45, the chemical structure (4) should read:

(4)

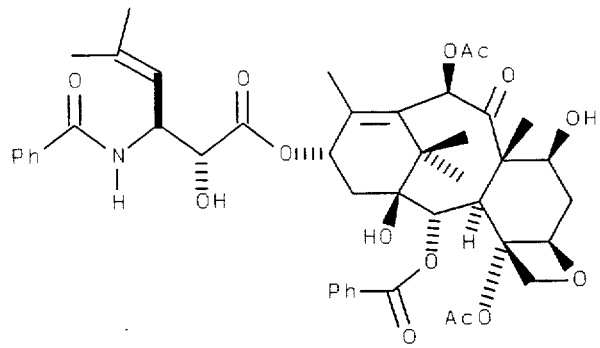

In Claim 2, column 10, line 11, " $(CH_2)_nN\oplus R^6R^7R^8X\ominus$ " should read -- $(CH_2)_nN^{\oplus}R^6R^7R^8X^{\ominus}$ --.

In Claim 2, column 10, line 31, "$X\ominus$" should read -- $X^{\ominus}$ --.

In Claim 2, column 10, line 32, "$(HOC_2H_6)_3N$," should read -- $(HOC_2H_4)_3N$, --.

UNITED STATES PATENT AND TRADEMARK OFFICE
CERTIFICATE OF CORRECTION

PATENT NO. : 5,284,864

DATED : February 8, 1994

INVENTOR(S) : Robert A. Holton and Hossain Nadizadeh

It is certified that error appears in the above-identified patent and that said Letters Patent is hereby corrected as shown below:

In Claim 5, column 10, lines 42-54, the chemical structure (4) should read:

(4)

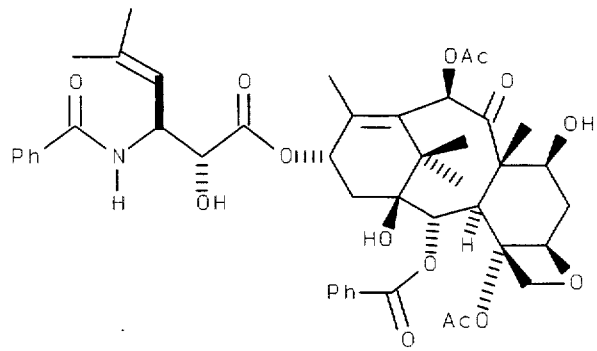

Signed and Sealed this

Tenth Day of February, 1998

Attest:

BRUCE LEHMAN

Attesting Officer

Commissioner of Patents and Trademarks